(12) United States Patent
Cantor (10) Patent No.: US 6,391,861 B1
(45) Date of Patent: *May 21, 2002

(54) METHOD FOR THE PREVENTION OF TISSUE ELASTIC FIBER INJURY

(75) Inventor: Jerome O. Cantor, Bronx, NY (US)

(73) Assignee: The Trustees of Columbia University in the City of New York, New York, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/079,209

(22) Filed: May 14, 1998

(51) Int. Cl.[7] ........................ A61K 31/715; A07N 43/04
(52) U.S. Cl. ............................ 514/54; 514/59; 514/21; 514/2; 424/422; 424/423; 424/424; 424/425; 530/350; 530/356; 530/857; 604/289; 604/290; 604/304; 604/306; 604/307
(58) Field of Search .................................. 514/2, 21, 54, 514/59; 424/422, 423, 424, 425; 530/350, 356, 857; 604/289, 290, 304, 306, 307

(56) References Cited

U.S. PATENT DOCUMENTS

| | | |
|---|---|---|
| 4,725,585 A | 2/1988 | Wenge et al. |
| 4,925,678 A | 5/1990 | Ranney |
| 5,633,003 A | 5/1997 | Cantor |
| 5,707,604 A | 1/1998 | Ranney |
| 5,767,106 A | 6/1998 | Turley et al. |
| 5,872,109 A | 2/1999 | Akima et al. |
| 5,929,048 A | 7/1999 | Falk et al. |
| 5,990,096 A | 11/1999 | Asculai et al. |
| 5,993,783 A | 11/1999 | Eljamal et al. |

FOREIGN PATENT DOCUMENTS

WO    WO 95/26735    10/1995

OTHER PUBLICATIONS

Cantor, J.O et al., (1993) "Pulmonary Air–Space Enlargement Induced by Intratracheal Instillment of Hyaluronidase and Concomitant Exposure to 60% Oxygen", *Exper. Lung Res.* 19:177–192 (Exhibit 3)

Rao, N.V. et al., (1990) "Sulfated Polysaccharides Prevent Human Leukocyte Elastase–induced Acute Lung Injury and Emphysema in Hamsters" *Am. Rev. Respir. Dis.* 142:407–412 (Exhibit 4).

Walsh, R.L. et al., (1991) "Heparin and Heparan Sulphate are Inhibitors of Human Leucocyte Elastase", *Clin. Sci.*, 81:341–346 (Exhibit 5).

Bray, B.A. et al., (1994) "Lung Hyaluronan as Assayed with a Biotinylated Hyaluronan–Binding Protein", *Exper. Lung Res.*, 20:317–330, (Exhibit 1).

Cantor, J.O. et al., (1995) "Modulation of Airspace Enlargement in Elastase–Induced Emphysema by Intratracheal Instillment of Hyaluronidase and Hyaluronic Acid". *Exper. Lung Res.*, 21:423–436. (Exhibit 2).

The Japanese version of Ishibashi, M., et al. (1995) "The Role of Interstitial Hyaluronan in Acute Lung Injury" *Japanese Journal of Thoracic Disease* 33(Suppl):225–230 (Exhibit 4); and Abstract by Murakami, H.,et al. (Jul. 1998) "Effect of hyaluronidase on porcine pancreatic elastase–induced lung injury" 36(7):577–584 (Exhibit 5).

Abstract by Ishibashi M., et al. (Dec. 1995) "The role of interstitial hyaluronan in acute lung injury" 33 (Suppl):225–230 (Exhibit 2).

An English translation of Ishibashi, M., et al. (1995) "The Role of Interstitial Hyaluronan in Acute Lung Injury" *Japanese Journal of Thoracic Disease* 33(Suppl):225–230 (Exhibit 3).

Baba, Tooru, et al., "Ultrastructural Cytochemistry of Carbohydrates in Microfibrils Associated with the Amorphous Elastin in the Monkey Aorta" *The Anatomical Record* (1985) vol. 213:385–391 (Exhibit 1).

Baccarani–Contri, Miranda, et al., "Elastin–Proteoglycans Association Revealed by Cytochemical Methods" *Connective Tissue Research* (1985) vol. 13:237–249 (Exhibit 2).

Baccarani–Contri, Miranda, et al., "Immunocytochemical Localization of Proteoglycans Within Normal Elastin Fibers" *European Journal of Cell Biology* (1990) vol. 53:305–312 (Exhibit 3).

Cantor, Jerome O., et al., "Further Investigation of the Use of Intratracheally Administered Hyaluronic Acid to Ameliorate Elastase–Induced Emphysema" *Experimental Lung Research* (1997) vol. 23:229–244 (Exhibit 4).

Cantor, Jerome O., et al., "Aerosolized Hyaluronic Acid Decreases Alveolar Injury Induced by Human Neutrophil Elastase" *P.S.E.B.M.* (1998) vol. 217:471–475 (Exhibit 5); and (List continued on next page.)

Primary Examiner—James O. Wilson
(74) Attorney, Agent, or Firm—Bryan Cave LLP (57) ABSTRACT

The subject invention is directed to the prevention of elastic fiber injury by administering HA or any other polysaccharide or carbohydrate moiety that binds to and coats elastic fibers, thereby preventing enzymes, oxidants, or other injurious agents from contacting and damaging these fibers. The method may be used to prevent elastic fiber damage which occurs to the skin and blood vessels as a consequence of aging, to the uterus during pregnancy, and in diseases such as pulmonary emphysema, aortic aneurysm, and joint disease. The treatment is intended for humans and a variety of other mammals. The polysaccharide or carbohydrate moiety may be administered orally, cutaneously, subcutaneously, intravenously, intratracheally, or by any other route deemed efficacious. It may be administered alone or in combination with another polysaccharide or carbohydrate moiety, with or without a carrier such as saline solution, DMSO, alcohol or water. It may be naturally occurring, chemically modified, or artificially synthesized. The effective daily amount of the polysaccharide or carbohydrate moiety is from about 0.1 µg/kg to about 1 mg/kg of body weight.

8 Claims, 10 Drawing Sheets

OTHER PUBLICATIONS

Erlinger, Rainer, "Glycosaminoglycans in Porcine Lung: An Ultrastructural Study Using Cupromeronic Blue" *Cell Tissue Research* (1995) vol. 281:473–483 (Exhibit 6).

Cantor, J., et al., "Synthesis of Crosslinked Elastic by a Mesothelial Cell Culture," Proceedings of the Society for Experimental Biology and Medicine, vol. 181, pp. 387–391 (1986).

Lafuma, C., et al., "Biosynthesis of Hyaluronic Acid, Heparan Sulfate and Structural Glycoproteins in Hamster Lung Explants during Elastase Induced Emphysema", Connective Tissue Research, vol. 13, pp. 169–179 (1985).

Osman, M., et al., "Cigarette Smoke Impairs Elastin Resynthesis in Lungs of Hamsters with Elastase–induced Emphysema", Am. Rev. Respir, Dis., vol. 132, pp. 640–643 (1985).

Campbell, E., et al., "Relative Importance of Cell–Substrate Contact and Oxidative Inactivation of Proteinase Inhibitors in Vitro", J. Clin, Invest., vol. 70, pp. 845–852 (1982).

Toole, B., "Gylycosaminoglycans in Morphogenesis", Cell Biology of Extracellular Matrix, New York, Plenum, chapter 9, pp. 259–294.

Chrzanowski, P., et al., "Elastin Content of Normal and Emphysematous Lung Parenchyma", The American Journal of Medicine, vol. 69, pp. 351–359 (Sep. 1980).

Maczar, M., et al., "Glycosaminoglycans in Elastase Induced Emphysema", Bull. europ. Physiopath.resp., vol. 16 (suppl), pp. 99–104 (1980).

de Belder, A., et al., "Preparation and Properties of Fluorescein–Labelled Hyaluronate", Carbohydrate Research, vol. 44, pp. 251–257 (1975).

Montomiya, M., et al., "Über Glykosaminoglykane bei einem Fall von Lungenemplyhsem", Z. Erkr. Atm., vol. 143, pp. 270–276 (1975).

Laurell, C.–B., et al., "The Electrophoretic a1–Globulin Pattern of Serum in a1–Antitrypsin Deficiency", Scandinav. J. Clin. & Lab. Investigation, vol. 15, pp. 32–140 (1963).

Bhattacharya, J., et al., "Hyaluronan affects extravascular water in lungs of unanesthetized rabbits", J.Appl. Physiol., vol. 66, pp. 2595–2598 (1989).

Zimmerman, M., et al., "Design and Properties of Synthetic Elastase Inhibitors", Elastin and Elastases, vol. II, chapter 12, pp. 109–123.

Senior, R., et al., "The Pathogenesis of Emphysema", Pulmonary Diseases and Disorders, 2d ed., New York, McGraw–Hill, chapter 74, pp.1 209–1218 (1988).

Page, C., "Proteoglycans: The "Teflon"of the airways?", Thorax, The Journal of the British Thoracic Society, vol. 52, No. 10, pp. 924–925 (1997).

Pare, P., et al., "The functional consequences of airway remodelling in asthma", Damage and Remodelling in Airway Inflammation, vol. 52, No. 6, pp. 589–596 (1997).

Rosenbaum, D., "Hyaluronan in Radiation–Induced Lung Disease in the Rat", Radiation Research, vol 147, pp. 585–591 (1997).

Akima, K., et al., "Evaluation of Antitumor Activities of Hyaluronate Binding Antitumor Drugs: Synthesis, Characterization and Antitumor Activity", Journal of Drug Targeting, vol. 4, pp. 1–8 (1996).

Pruimboom, I., et al., "Capsular Hyaluronic Acid–mediated Adhesion of *Pasteurella multocida* to Turkey Air Sac Macrophages", Avian Diseases, vol. 40, pp. 887–893 (1996).

Sköld, C., et al., "Transient increases in albumin and hyaluronan in bronchoalveolar lavage fluid after quitting smoking: possible signs of reparative mechanisms", Respiratory Medicine, vol. 90, pp. 523–529 (1996).

Juul, S., et al., "Hyperoxia Alone Causes Changes in Lung Proteoglycans and Hyaluronan in Neonatal Rat Pups", American Journal of Respiratory Cell and Molecular Biology, vol. 13, pp. 629–638 (1995).

Song, W.D., et al. "Fibronectin and Hyaluronan in Bronchoalveolar Lavage Fluid from Young Patients with Chronic Obstructive Pulmonary Diseases", Respiration, vol. 62, pp. 125–129 (1995).

Teder, P., et al., Characterization of the Mechanism Involved in Bleomycin–induced Increased Hyaluronan Production in Rat Lung: American Journal of Respiratory Cell and Molecular Biology, vol. 12, pp. 181–189 (1995).

Aviad, A., et al., "The Molecular Weight of Therapeutic Hyaluronan (Sodium Hyaluronate): How Significant is it?", The Journal of Theumatology, vol.21, pp. 297–301 (1994).

Gandhi, R., et al., "Analysis of elastin cross–linking and the connective tissue matrix of abdominal aortic aneurysms", Surgery, vol. 115, pp. 617–620 (May 1994).

Juul, S., et al., "Changes in Hyaluronan Deposition during Early Respiratory Distress Syndrome in Premature Monkeys", Pediatric Research, vol. 35, No. 2, pp. 238–243 (1994).

Townsley, M., et al., "Hyaluronan Efflux from Canine Lung with Increased Hydrostatic Pressure and Saline Loading", American Journal of Respiratory and Critical Care Medicine, vol. 150, pp. 1605–1611 (1994).

Goldberg, E., et al., "Prevention of Postoperative Adhesions by Precoating Tissues with Dilute Sodium Hyaluronate Solutions", Prog. Clin. Biol. Res., vol. 381, pp; 191–204 (1993).

Graf, J., et al., "Intra–articular treatment with hyaluronic acid in osteoarthritis of the knee joint: a controlled clinical trial versus mucopolysaccharide polysulfuric acid ester", Clinical and Experimental Rheumatology, vol. 11, pp. 367–372 (1993).

Leardini, G., et al., "Intra–articular treatment of knee osteoarthritis. A comparative study between hyaluronic acid and 6–methyl prednisolone acetate", Clinical and Experimental Rheumatology, vol. 9, pp. 375–381 (1991).

Nettelbladt, O., et al., "Alveolar accumulation of hyaluronan and alveolar cellular response in bleomycin–induced alveolitis", Eur. Respir. J., vol. 4, pp. 407–414, (1991).

Cantor, J. et al., "The Effect of 60% Oxygen on Air–space Enlargement and Cross–linked Elastin Synthesis in Hamsters with Elastase–induced Emphysema", Am. Rev. Respir. Dis., vol. 142, pp. 668–673 (1990).

Shteyngart, B., et al., "Preferential binding of lysozyme to elastic fibres in pulmonary emphysema", Thorax, vol. 53, pp. 193–196 (1998).

Tyrrell, D., et al., "Heparin in Inflammation: Potential Therapeutic Applications beyond Anticoagulation", Adv. Pharmacol., vol. 46, pp. 151–208 (1999).

Feng, W., et al., "Improved Clearability of Cystic Fibrosis Sputum with Dextran Treatment in vitro", Am. J. Respir. Crit. Care Med., vol. 157, pp. 710–714 (1998).

Barnes, P., et al., "Inflammatory Mediators of Asthma: An Update", Pharmacological Reviews, vol. 50, No. 4, pp. 515–596 (1998).

Cantor, J., Abstract for "Intratracheal Instillment of Hyaluronic Acid Decreases Elastase–Induced Air–Space Enlargement in Hamsters", Exper. Lung Res., vol. 19, pp. 177–192 (1993).

METHOD FOR THE PREVENTION OF TISSUE ELASTIC FIBER INJURY

Throughout this application, various publications are referenced by numbers. The full citations are listed at the end of the specification immediately preceding the claims.

BACKGROUND OF THE INVENTION

Elastic fibers are a prominent component of the extracellular matrix and play an important role in determining the mechanical properties of tissues. By virtue of their distensibility, elastic fibers permit tissues to function normally despite the application of external forces. In the lung, for example, interstitial and pleural elastic fibers facilitate tissue recoil following inspiration, preventing permanent distention of the organ and maintaining the flow of gases within airways. Damage to these fibers causes dilatation and rupture of alveoli, resulting in pulmonary emphysema (1,2).

Despite the importance of maintaining the integrity of elastic fibers, there is currently no effective means of protecting them from damage. Since these fibers are susceptible to degradation by enzymes known as elastases, various elastase inhibitors have been tested as a possible means of preventing elastic fiber injury (1,3). In particular, a naturally occurring inhibitor, alpha-1-antiproteinase, has recently been given to individuals who normally lack this inhibitor in an attempt to slow the progression of elastic fiber breakdown which leads to pulmonary emphysema (4). Such a treatment strategy assumes, however, that elastic fiber injury is caused by a specific type of biochemical derangement, i.e. alpha-1-antiproteinase deficiency. If damage to these fibers represents a more general reaction to a variety of insults (with elastases playing a variable role), then enzyme inhibition may have only limited efficacy.

To determine if mechanisms other than elastase injury are involved in elastic fiber breakdown, a series of experiments were performed by this laboratory involving both the induction and modification of experimental emphysema with agents other than elastases. Experiments using hyaluronidase and 60 percent oxygen showed that significant damage to elastic fibers occurs only when both agents are given concomitantly, suggesting the possibility that hyaluronidase may facilitate the breakdown of elastic fibers by making them more accessible to injury (5). This hypothesis was further tested by giving hamsters intratracheal instillments of hyaluronidase, followed by elastase, and then examining the lungs for air-space enlargement (6). The findings indicated that pretreatment with hyaluronidase enhances elastase-induced emphysema. Furthermore, it was found that intratracheally administered hyaluronic acid (HA) had the opposite effect, significantly reducing elastase-induced air-space enlargement. This latter finding resulted in a U.S. patent on the use of intratracheally administered HA to ameliorate emphysema (5,663,003). The current application describes the underlying mechanism responsible for the protective effect of HA, which was previously unknown, and the methods described below are specifically directed to the prevention of injury to tissue elastic fibers.

As will be shown, the protective effect of HA does not involve inhibition of elastase, but instead depends upon direct interaction with elastic fibers. Both in vivo and in vitro studies using fluorescein-labeled HA, indicate that this polysaccharide preferentially binds to and coats elastic fibers, protecting them from injury. Such binding may be related to the numerous carboxyl and hydroxyl groups within HA which are possibly attracted to elastic fibers by one or more of the following mechanisms: 1) hydrogen bonds, 2) electrostatic bonds, or 3) van der Waals forces. Since many polysaccharides or other carbohydrate moieties share similar chemical properties, it may be possible to use them in a like manner to coat elastic fibers.

SUMMARY OF THE INVENTION

The subject invention is directed to the prevention of injury to mammalian tissue elastic fibers by administration of HA or any other polysaccharide or carbohydrate moiety that binds to and coats elastic fibers, thereby protecting these fibers from enzymes, oxidants, or other injurious agents. Studies by the inventor (JOC) have shown that HA preferentially binds to elastic fibers in the lung and prevents destruction of alveoli by intratracheally administered elastases. Corresponding in vitro experiments demonstrate that binding of HA to elastic fibers interferes with the ability of elastase to damage the fibers. Since other polysaccharides share similar chemical properties with HA, it may be possible to use them in a like manner to coat elastic fibers. Consequently, the invention comprises all forms of naturally occurring, chemically modified, or artificially synthesized compounds which are wholly or partially composed of polysaccharides or other carbohydrate moieties and which are capable of covalently or noncovalently binding to elastic fibers. Such compounds could be administered orally, subcutaneously, intravenously, intratracheally, or by any other route deemed efficacious. They may be administered alone or with a carrier such as saline solution, DMSO, alcohol, or water. The effective daily amount of the compound(s) is from about 0.1 $\mu$g/kg to about 1 mg/kg body weight.

BRIEF DESCRIPTION OF THE FIGURES

FIG. 8: (Upper Left) Cultured rat pleural mesothelial cells showing characteristic polygonal shape; (Upper Right) Phase-contrast photomicrograph demonstrating prominent extracellular matrix, which appears black; (Lower Left) Fluorescence photomicrograph of cell-free rat pleural mesothelial matrix following incubation with fluorescein-labeled HA (1 mg/ml) for 10 min. Note preferential binding of fluorescein-HA to extracellular matrix; (Lower Right) Following exposure of cell-free matrix to porcine pancreatic elastase (100 ng/ml) for 1 hr, much of the fluorescein-HA is removed. However, residual fluorescence indicates that the matrix remains largely intact. The elastase-induced loss of fluorescence suggests that HA preferentially binds to elastic fibers.

DETAILED DESCRIPTION OF THE INVENTION

The subject invention is directed to prevention of mammalian tissue elastic fiber injury by administration of HA or any other polysaccharide or carbohydrate moiety that binds to and coats elastic fibers, thereby preventing enzymes, oxidants, other injurious agents, genetic abnormalities, or the effects of aging from damaging these fibers.

As used herein, polysaccharide is defined as a carbohydrate containing many saccharide units (i.e. sugars with the general composition of $(CH_2O)_n$ and simple derivatives thereof). The sugars may contain amino and sulfate groups as in glycosaminoglycans (e.g. chondroitin sulfate, dermatan sulfate, and heparan sulfate).

Carbohydrate moiety is defined as a group of compounds consisting of small molecules such as mono-and disaccharides as well as larger ones such as starch, glycogen, and cellulose. Generally, they conform to the formula $C_n(H_2O)_n$.

Enzymes are enzymes capable of degrading elastic fibers such as elastases.

Oxidants include oxidants involved in tissue and/or elastic fiber injury which include but are not limited to, ozone, superoxide anion, hydrogen peroxide, hydroxyl radical, hypochlorous acid, monochloramine, nitrogen dioxide, and peroxyl radical.

Other injurious agents include ultraviolet radiation, infectious agents, and toxic substances, (e.g. insecticides, exhaust fumes, and chemotherapeutic agents). Genetic abnormalities include alpha-1 -antiproteinase deficiency and other types which impair elastic fiber synthesis or promote elastic fiber degradation.

In an embodiment of the above method, the polysaccharide or carbohydrate moiety is bound to a carrier molecule. In a further embodiment, the carrier molecule is a protein. Examples of the carrier molecule are the elastin receptor molecule and CD44 receptor. An example of the carrier protein is the link protein associated with HA.

The treatment is intended for a variety of mammals including humans. It may be useful in preventing the elastic fiber damage that occurs to skin and blood vessels during the natural process of aging, to the uterus during pregnancy, and in diseases such as pulmonary emphysema, aortic aneurysm, solar elastosis of the skin, and joint disease.

The polysaccharide or carbohydrate moiety may be administered orally, intravenously, cutaneously, subcutaneously, intratracheally, intramuscularly, by anal suppository application, by internal topical application or by any other route deemed efficacious. It may be administered alone or in combination with other polysaccharides or carbohydrate moieties, with or without a suitable carrier. Such suitable carriers include, but are not limited to carrier like saline solution, DMSO, alcohol, or water. It may be composed of naturally occurring, chemically modified, or artificially synthesized compounds which are wholly or partially composed of polysaccharides or other carbohydrate moieties, and which are capable of binding covalently or noncovalently to elastic fibers. As shown below, the ability of a compound to bind to elastic fibers can be demonstrated by fluorescence microscopy, following conjugation of the compound with a fluorescent dye.

The amount of the polysaccharide or carbohydrate moiety administered daily may vary from about 0.1 µg/kg to about 1 mg/kg of body weight, depending on the site and route of administration. To coat hamster lung elastic fibers with HA, for example, a 50 minute exposure to an aerosol containing a 0.1 percent solution of bovine tracheal HA in water (1 mg/ml) was used.

This invention will be better understood from the Experimental Details which follow. However, one skilled in the art will readily appreciate that the specific methods and results discussed are merely illustrative of the invention as described more fully in the claims which follow thereafter.

Experimental Details

Effect of HA on Pulmonary Emphysema Induced by Pancreatic Elastase:

Measurements of air-space size were performed 1 week after intratracheal instillments of elastase and HA or elastase and saline. As shown in FIG. 1, animals given 1 mg of HA immediately following elastase administration showed a marked reduction in air-space enlargement compared to those secondarily receiving saline (82 vs 122 $\mu$m). Histological examination of the lungs from both treatment groups showed minimal inflammatory changes composed of scattered intraalveolar collections of neutrophils and red blood cells. No specific changes were associated with the added administration of HA.

Animals instilled with 1 mg of HA, 2 hrs preceding elastase, had a significantly lower mean linear intercept than controls receiving saline, then elastase (96 vs 120 $\mu$m; $p<0.05$; FIG. 1). A further reduction in airspace enlargement was seen with 2 mgs of HA, which resulted in a mean linear intercept of 88 $\mu$m ($p<0.05$ vs controls; FIG. 1).

Instillment of 2 mgs of HA, 1 hr after elastase, also resulted in a significant decrease ($p<0.05$) in air-space enlargement (66 vs 104 $\mu$m; FIG. 1). However, 1 mg of HA, given either 1 or 2 hrs after elastase administration, did not significantly affect the mean linear intercept (treated vs control: 100 vs 104 $\mu$m at 1 hr, 114 vs 124 $\mu$m at 2 hrs; FIG. 1).

These results indicate that HA ameliorates elastase-induced emphysema. Furthermore, they suggest that the protective effect of HA may involve early events in the development of the experimental injury which precede elastic fiber breakdown. Since this laboratory has already shown that HA has no elastase inhibitory capacity (6), the decrease in lung injury may possibly be related to indirect effects between the polysaccharide and elastase, such as reduction of enzyme mobility within the lung interstitium, or, alternatively, direct interactions between HA and elastic fibers themselves.

Effect of HA on Emphysema Induced by Neutrophil Elastase:

Two hours prior to intratracheal instillment of 40 units of human neutrophil elastase, animals were given either 1, 2, or 4 mgs of HA via the same route. Compared to controls receiving saline alone, all groups administered HA showed a decreased mean linear intercept (FIG. 2). The values were significantly lower ($p<0.05$) in animals receiving 1 and 4 mgs of HA (57 and 59 µm, respectively, vs 64 µm for controls). In contrast to pancreatic elastase-induced emphysema, there was no correlation between the amount of HA instilled and the degree of reduction in mean linear intercept. This is not surprising in view of the fact that neutrophil elastase is less effective than its pancreatic counterpart in producing air-space enlargement. The mean linear intercept measurements seen with HA treatment are close to normal values, which range from 50–60 µm, based on previous determinations (5,6).

Figure 3:
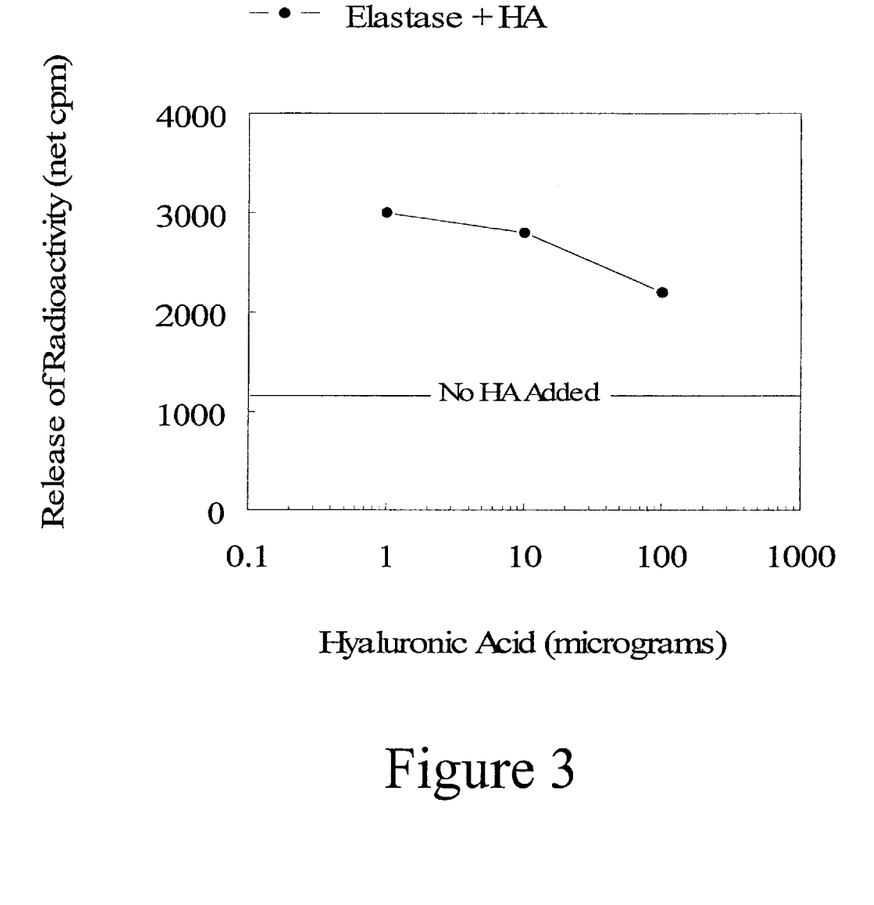
FIG. 3: Incubation of hyaluronic acid with elastase increases, rather than reduces, degradation of elastin, as measured by release of radioactivity from $^3$H-elastin substrate. Thus, HA has no elastase inhibitory capacity.

Effect of HA on Elastase Activity:

Incubation of HA with pancreatic elastase did not reduce $^3$H-elastin breakdown, but instead caused an increase in the release of radioactivity from the substrate (FIG. 3). This stimulatory effect may result from greater interaction between enzyme and substrate (possibly due to alteration of electrostatic binding).

Characterization of HA Preparation:

The average molecular weight of the commercial bovine tracheal HA used in all the experiments described above was 104,800, based on intrinsic viscosity measurements (table 1).

TABLE 1

Chemical and Physical Characteristics of Bovine tracheal HA

| Uronic Acid (ug/ml) | Hexosamine (ug/ml) | Protein (%)* | Intrinsic Viscosity (cc/gm) | MW. (Daltons) |
|---|---|---|---|---|
| 94.0 | 93.8 | 4.6 | 292 | 104,800 |

Ration of UA/Hexosamine = 1.0
*Percentage of protein calculated on the basis of HA content.

Figure 4:
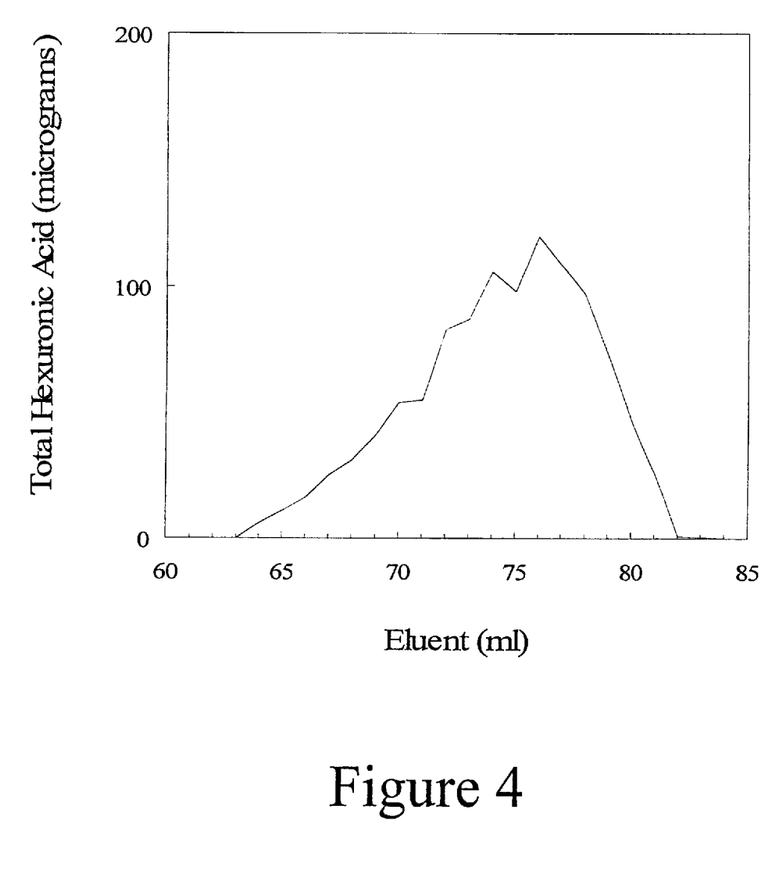
FIG. 4: Chromatographic separation of bovine tracheal HA on Sephacryl S-500 gel column.

This value is relatively low compared to other preparations of HA, some of which may have molecular weights in excess of 3×10$^6$. The material tested was relatively pure, containing less than 5 percent protein, and the uronic acid to hexosamine ratio was 1.0, which is characteristic of HA. Gel filtration chromatography revealed a broad elution profile (FIG. 4), containing polysaccharide chains of varying lengths, a feature commonly observed with HA preparations.

Preparation of Fluorescein-Labeled HA:

Fluorescein amine was coupled to bovine tracheal hyaluronic acid, according to previously published techniques (7). A solution of 100 mgs of HA in 80 ml water was diluted with 40 ml dimethyl sulfoxide and combined with acetaldehyde (50 µl), cyclohexyl isocyanide (50 µl), and fluorescein amine (50 mgs). The mixture was incubated at 22° C. for 5 hrs and the resultant fluorescein-labeled HA was isolated by alcohol precipitation and gel filtration. Thin-layer chromatography was used to determine the purity of the preparation.

Studies Using Fluorescein-Labeled HA:

Female Syrian hamsters, weighing approximately 100 gms each, were instilled intratracheally with 2 mgs of the fluorescein-labeled HA (in 0.2 ml saline solution), according to procedures described above. At 1, 2, 4, 24, and 72 hrs following instillment, the animals were sacrificed and their lungs were prepared for histology. Unstained slide sections were then prepared and subjected to fluorescence microscopy. Sections were also stained for elastic fibers (Verhoeff-Van Gieson stain) and examined with a light microscope.

Figure 5:
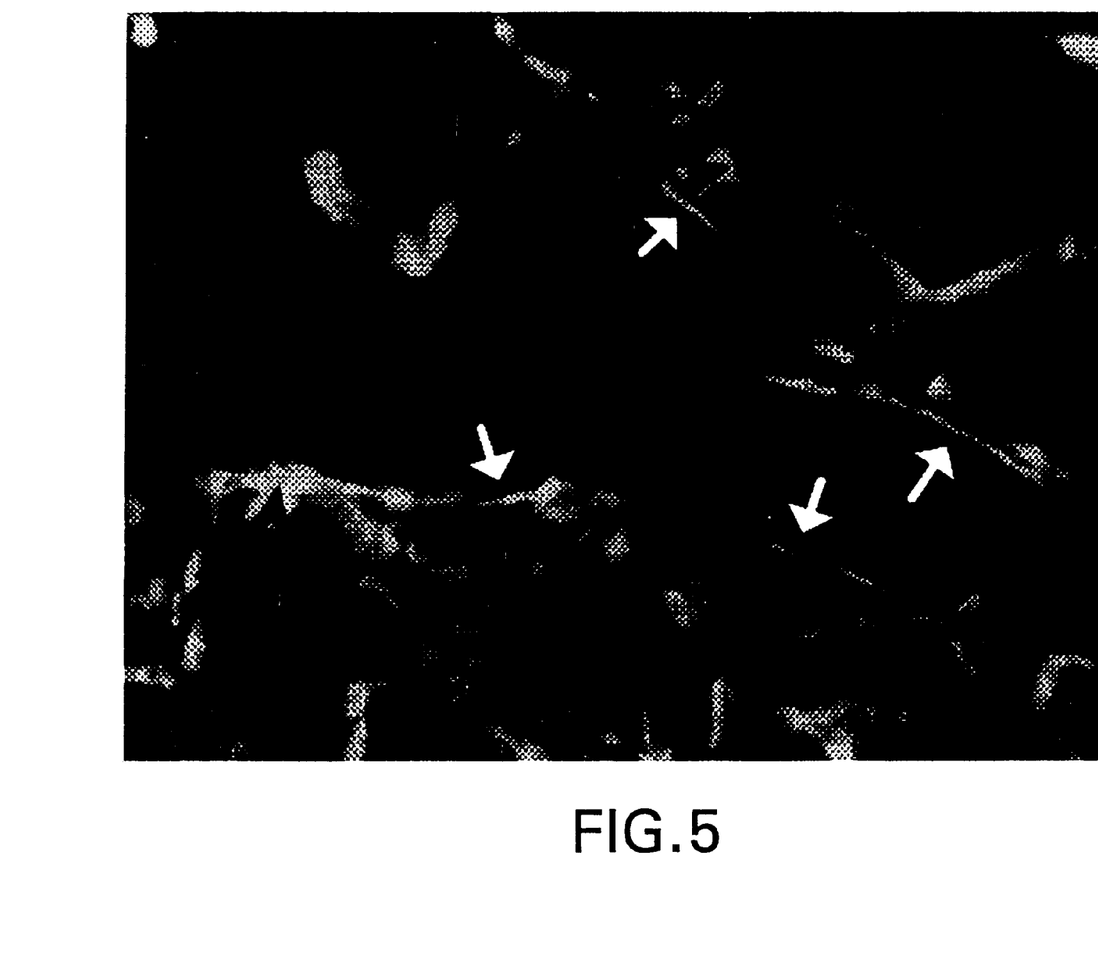
FIG. 5: High-power view of fluorescent elastic fibers in alveolar septa (arrowheads), 1 hr after instillment of fluorescein-labeled HA. (Original magnification: ×790)
Figure 6:
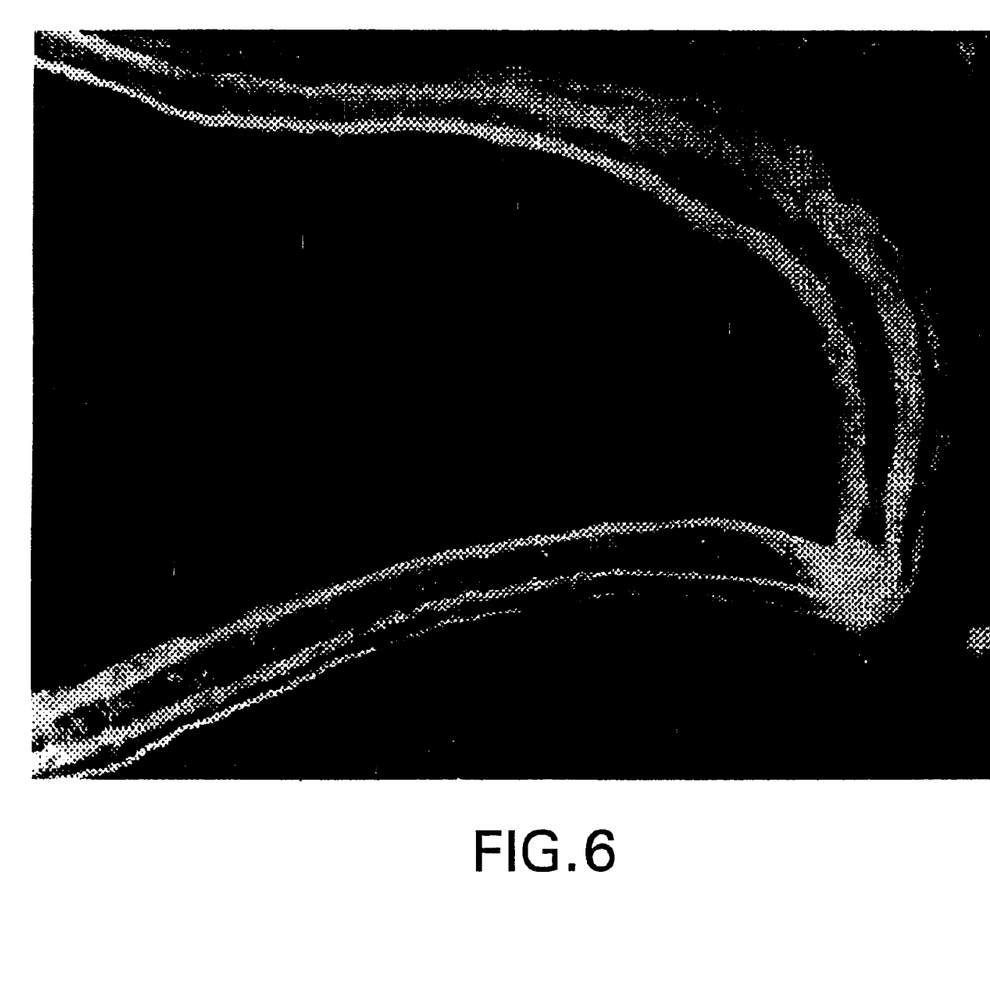
FIG. 6: Elastic fibers in a large pulmonary blood vessel show prominent fluorescence, 2 hrs after instillment of fluorescein-labeled HA (Original magnification: ×250)

Fluorescence microscopy revealed a rapid influx of labeled HA into the lung. Since the labeled HA was instilled intratracheally, its distribution was patchy. At 1, 2 and 4 hrs, there was prominent fluorescence associated with interstitial, pleural, and vascular elastic fibers (FIGS. 5,6). The identity of these fibers was confirmed with the Verhoeff-Van Gieson elastic tissue stain. Alveolar macrophages, which rapidly sequestered the labeled HA, also showed strong fluorescence.

By 24 hrs, overall fluorescence was significantly reduced, and much of the specificity for elastic fibers was missing. Alveolar macrophages, however, remained strongly fluorescent, even at 72 hrs.

Figure 1:
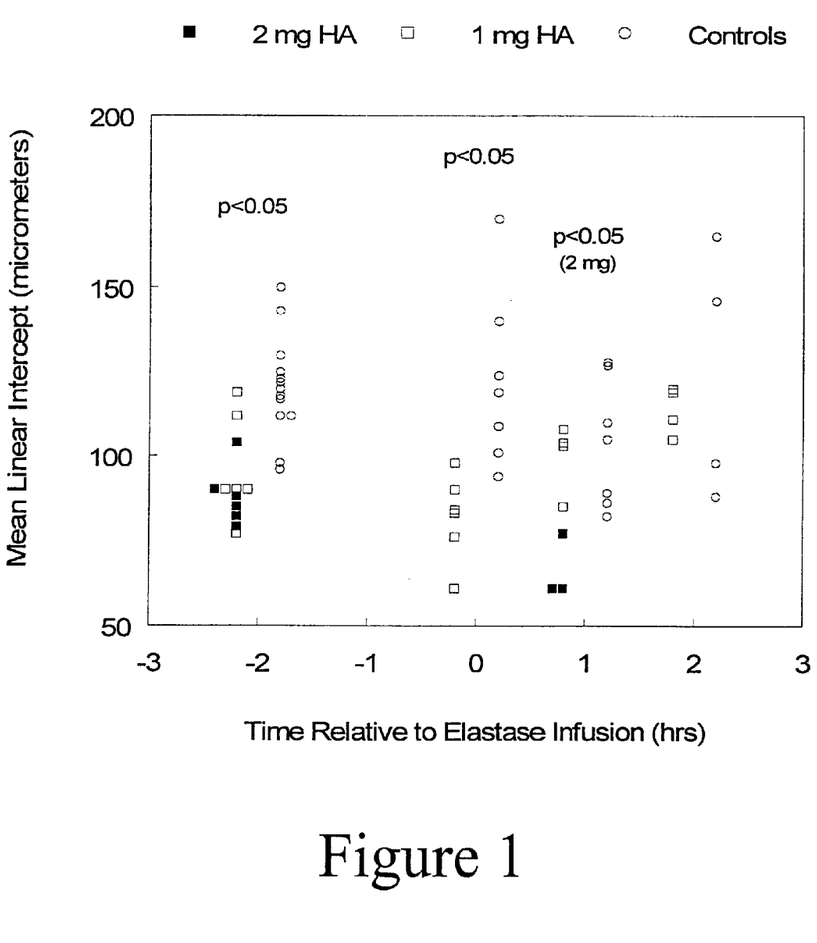
FIG. 1: HA exerts a protective effect on air-space enlargement when given at different times relative to pancreatic elastase.
Figure 2:
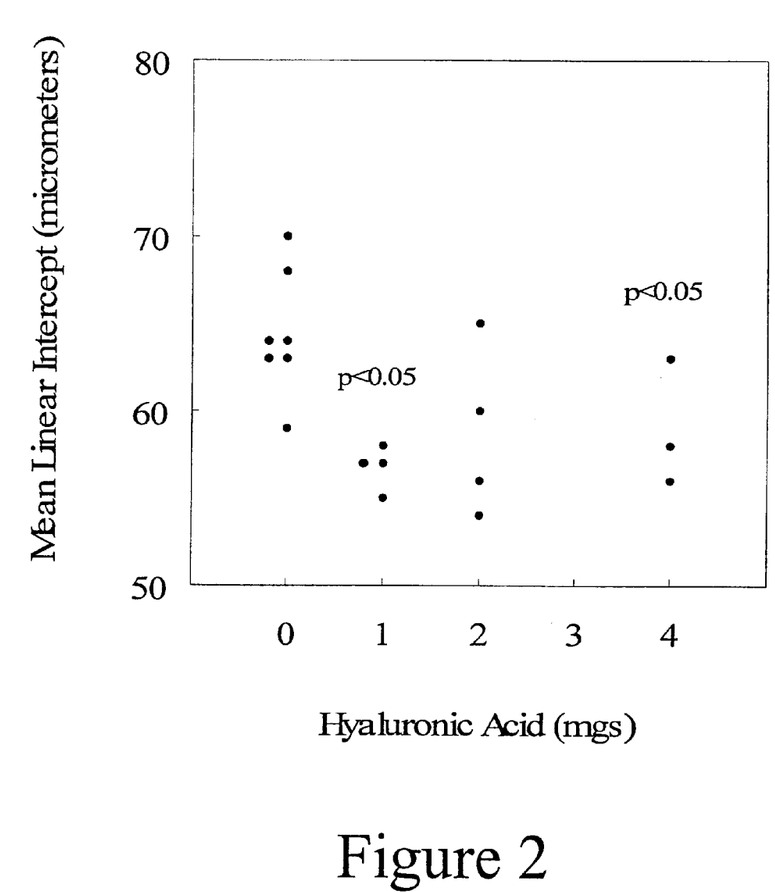
FIG. 2: HA exerts a protective effect on air-space enlargement when given 2 hrs prior to human neutrophil elastase.

The fluorescence associated with elastic fibers suggests that the lung may be protected from elastase injury by the temporary coating of these fibers with the instilled HA. This process appears to occur quickly and extend for at least 4 hours, explaining why air-space enlargement can be decreased by instilling HA either 2 hrs before or 1 hr after elastase administration (FIG. 1). The lack of protection observed when HA was instilled 2 hrs after elastase suggests that significant damage to elastic fibers may have occurred by this time (FIG. 1).

Aerosolization of HA:

Fluorescein-labeled HA (0.1 percent solution in water) was administered to hamsters using a nebulizer. After exposure to the aerosol for 50 minutes, the animals were sacrificed. Fluorescent microscopy of the lungs showed a more uniform distribution of fluorescent elastic fibers than that seen with intratracheally instilled fluorescein-HA, above. Furthermore, the aerosolized HA showed a protective effect against neutrophil elastase. Animals treated with an aerosol composed of 0.1% HA in water for 50 minutes, then instilled intratracheally with 80 units of neutrophil elastase, had a significantly lower mean linear intercept than controls treated with aerosolized water alone (68.2 µm vs 85.9 µm; p<0.05).

Figure 7:
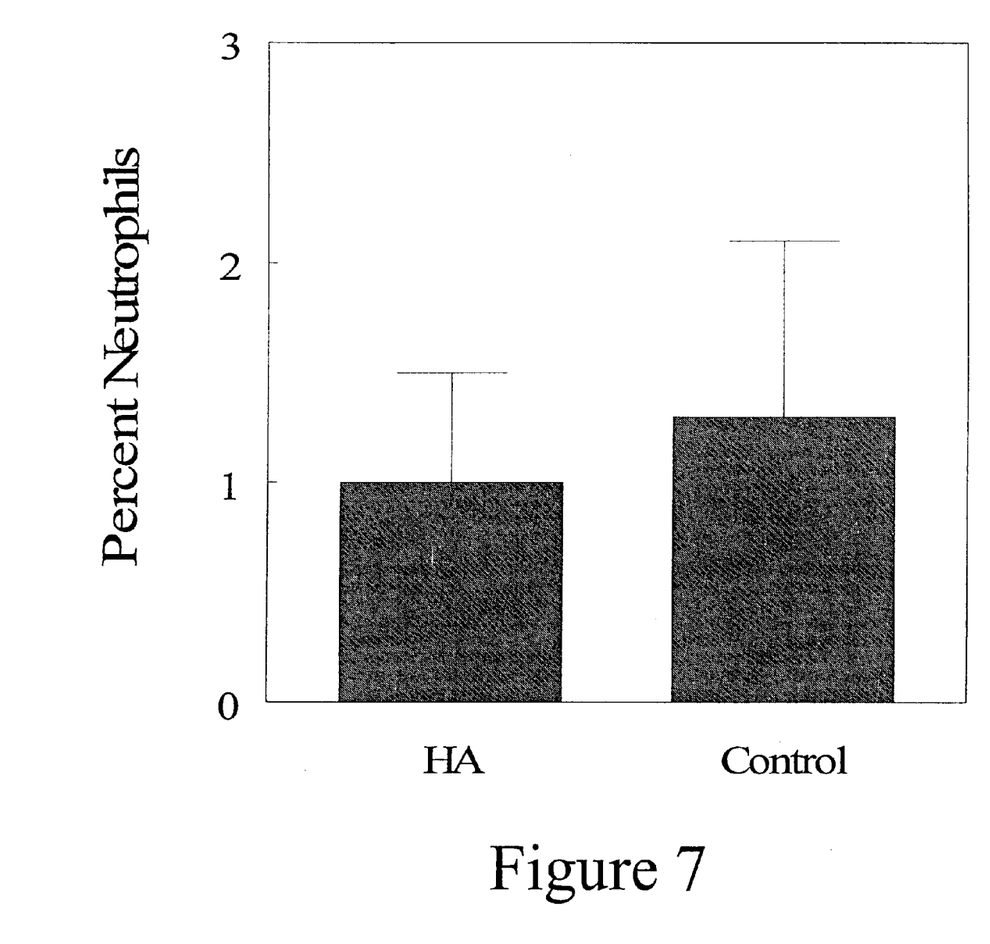
FIG. 7: The effect of aerosolized HA on the percentage of neutrophils in lung lavage fluid at 24 hrs. (N=3 for all groups; T-bars indicate SEM)

Possible inflammatory changes resulting from the aerosolized HA were determined by measuring the percentage of neutrophils in bronchoalveolar lavage fluid at 24 hours. Animals receiving HA showed no difference from controls exposed to aerosolized water for a similar time period (FIG. 7).

Prevention of Elastic Fiber Damage In Vitro:

Since HA has no elastase inhibitory capacity (6), the mechanism responsible for its protective effect needs to be clarified. Although HA has been shown to bind to elastic fibers, it remains to be determined if this actually prevents elastolysis. Such information is critically important in assessing the potential value of HA as a treatment for pulmonary emphysema and other diseases involving elastic fiber injury.

Figure 8A:
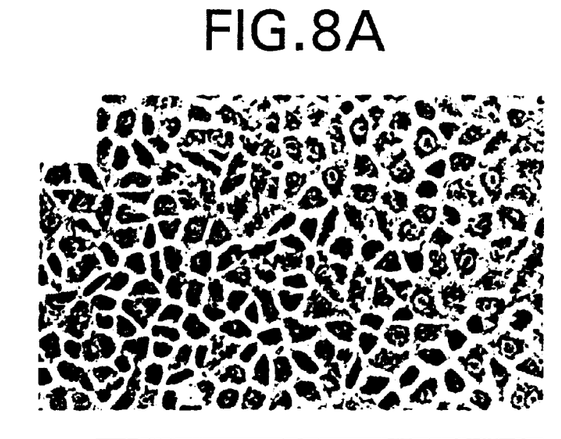
Figure 8B:
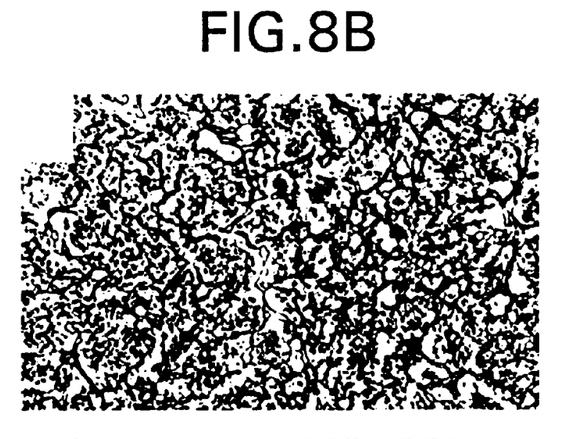

To address this issue, radiolabeled extracellular matrices, derived from cultured rat pleural mesothelial cells, were treated with HA and then incubated with porcine pancreatic elastase. The mesothelial cells have a polygonal appearance in culture (FIG. 8A) and produce a prominent extracellular matrix containing numerous elastic fibers (FIG. 8B). The cultures have previously been shown to synthesize abundant elastin, the primary component of these fibers (8). Radiolabeled matrices are prepared by incubating the cultures with $^{14}$C-lysine, then lysing the cells and removing them from the culture, leaving the residual extracellular matrix intact.

Figure 8C:
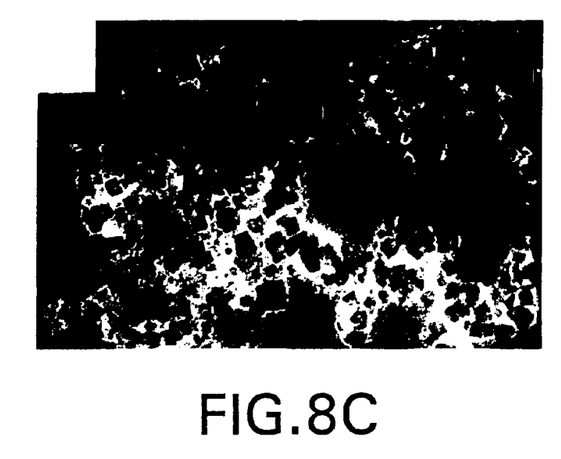
Figure 8D:
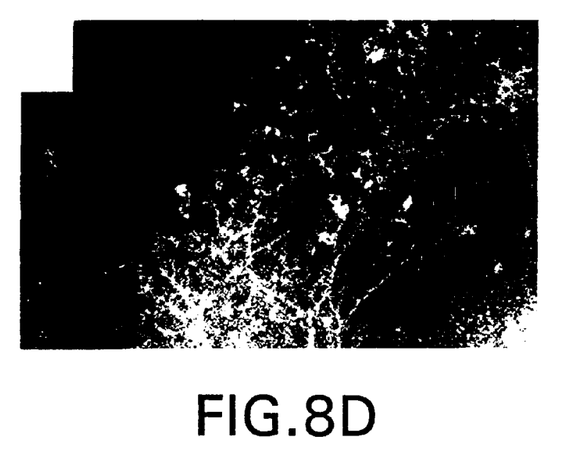

As shown by fluorescence microscopy (FIG. 8C), fluorescein-labeled HA binds to the mesothelial cell matrix. Following exposure of the matrices to porcine pancreatic elastase (100 ng/ml) for 1 hr, much of the fluorescein-HA is removed, but the remaining fluorescence indicates that the matrix is largely intact (FIG. 8D). The loss of fluorescence suggests that HA is specifically bound to elastic fibers.

Figure 9:
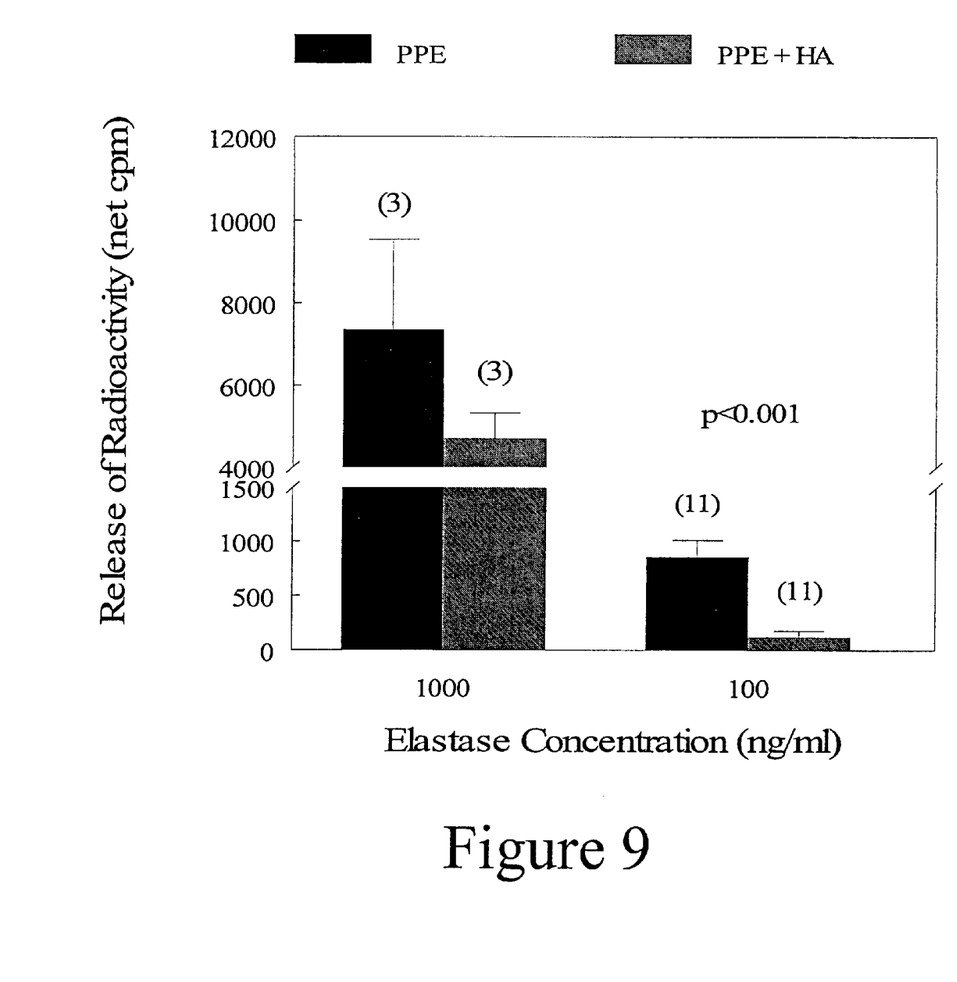
FIG. 9: Although pretreatment of the cell-free matrices with 1 mg/ml HA reduced the amount of radioactivity released by either 1 µg/ml or 100 ng/ml porcine pancreatic elastase, the protective effect was much more pronounced with the lower concentration of the enzyme ($p<0.001$). T-bars indicate SEM.

To determine if HA protects elastic fibers from injury, radiolabeled matrices were treated with 1 mg/ml of fluorescein-HA for 10 min, then incubated with either 1 µg/ml or 100 ng/ml elastase for 1 hr (FIG. 9). While release of radioactivity was reduced by HA at both concentrations of elastase, there was a much greater protective effect with 100 ng/ml of enzyme (855 vs 117 cpm; $p<0.001$). These results indicate that the loss of fluorescence following elastase treatment (FIG. 8D) is associated with minimal degradation of elastic fibers, suggesting that HA is only superficially bound to these fibers. It is unlikely that HA undergoes direct breakdown, since it is not a substrate for pancreatic elastase.

Figure 10:
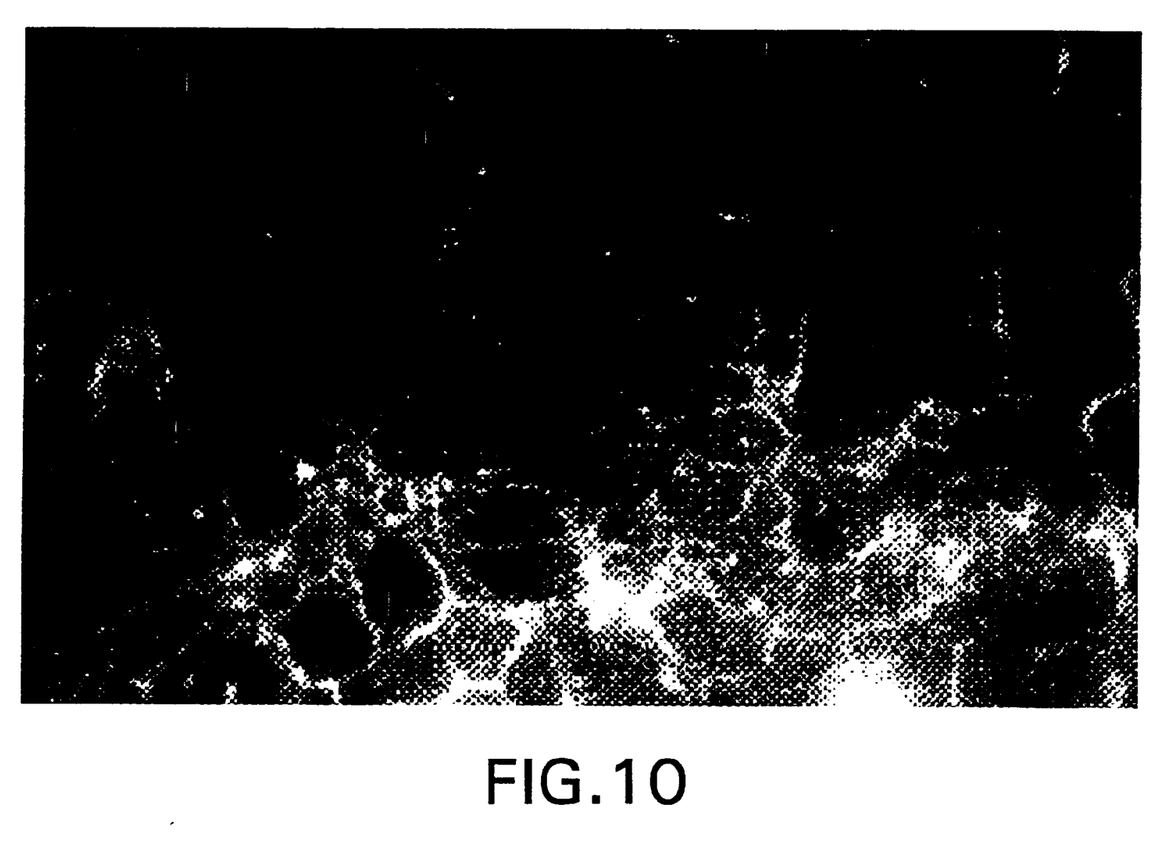
FIG. 10: Fluorescence photomicrograph showing binding of a second preparation of HA to rat pleural mesothelial cell elastic fibers. This shows that the protective effect of HA is not limited to a specific preparation of the material.

Testing the Efficacy of a Second Preparation of HA:

To determine if other forms of HA have a protective effect similar to the bovine tracheal preparation, a second form of HA was tested in vitro, using rat pleural mesothelial cell matrices. Streptococcal HA, produced by fermentation, was chemically modified to reduce its average molecular weight to approximately 100,000 (similar to the bovine tracheal HA used in all previous experiments). The new material was then conjugated to fluorescein (7) and tested for its ability to coat mesothelial cell elastic fibers. Fluorescence microscopy revealed a pattern similar to that seen with the bovine tracheal HA preparation (FIG. 10), demonstrating that other forms of HA may be equally effective in coating elastic fibers from injury.

Discussion of Findings:

In a previous study from this laboratory, in which hyaluronidase was found to synergistically interact with 60% oxygen to produce air-space enlargement, it was hypothesized that HA and other glycosaminoglycans may protect elastic fibers (5). Several studies support this concept by providing evidence that HA is closely associated with elastic fibers (9,10). Degradation of HA might therefore be necessary for elastases and cells, such as monocytes or neutrophils, to gain access to these fibers (11). As shown in a previous study from this laboratory, pretreatment of the lung with hyaluronidase resulted in an additional significant increase in air-space enlargement over that induced by intratracheal instillment of elastase alone (6).

The studies described above provide additional evidence that HA forms a complex with elastic fibers. The strong association of the fluorescein-labeled HA with elastic fibers clearly indicates that the instilled HA coats these fibers. Furthermore, studies using radiolabeled mesothelial cell matrices demonstrate that coating the elastic fibers with HA protects them from injury by elastase.

It has been shown that a loss of HA can reduce extravascular water content in the lung interstitium (12). Negatively charged carboxyl groups attached to the saccharide moieties repel one another, enlarging the domain of HA and enhancing its ability to entrap water (13). The hydrated and expanded HA may protect alveolar elastic fibers from contact with elastase.

The studies described above also addressed the question of whether HA is effective against neutrophil elastase, which has access to the lung parenchyma through neutrophil migration and secretion, as well as macrophage sequestering of the enzyme. In previous experiments, the use of intratracheally instilled HA was only tested against porcine pancreatic elastase, which experimentally produces more air-space enlargement than neutrophil elastase, but is not involved in the pathogenesis of human emphysema. The fact that HA is effective against neutrophil elastase increases the possibility that it may be useful in limiting alveolar damage occurring in emphysema. Furthermore, the ubiquity of neutrophil elastase in various lung inflammatory reactions suggests the possibility that HA may be effective against other forms of pulmonary injury as well.

As a possible treatment for pulmonary emphysema and other diseases involving elastic fiber injury, HA should well-tolerated by the lung and other organs. Studies from this laboratory, described above, have shown that aerosolization of HA does not cause pulmonary inflammation. Furthermore, HA has been administered to other tissues without adverse consequences (14–18). In contrast to elastase inhibitors, which are now being considered as therapeutic agents for emphysema, HA might provide a more direct form of lung protection with fewer potential side-effects.

Since many polysaccharides and other carbohydrate moieties share similar chemical properties with HA, it may be possible to use them in a like manner to coat elastic fibers. A family of "elastonic agents" might thus be developed with binding characteristics suited to individual tissue sites. The ability of a particular compound to bind to elastic fibers can be easily demonstrated by fluorescence microscopy, following conjugation of the compound with a fluorescent dye. Furthermore, the radiolabeled matrix preparation could be used to assess a compound's protective effect against elastic fiber injury. More sophisticated chemical techniques could then be used to determine specific binding characteristics.

REFERENCES

1. Janoff A: Elastases and emphysema: Current assessment of the protease-antiprotease hypothesis. Am Rev Respir Dis 132:417–433, 1985.
2. Senior R M, Kuhn C III: The pathogenesis of emphysema. In Fishman, A P (ed), Pulmonary Diseases and Disorders, 2d ed. New York, McGraw-Hill, pp. 1209–1218, 1988.
3. Zimmerman M, Powers J C: Design and properties of synthetic elastase inhibitors. In Elastin and Elastases, vol II, Robert L, Hornebeck W (eds), Boca Raton, CRC Press, pp 109–123, 1989.
4. Laurell C-B, Eriksson S: The electrophoretic $alpha_1$-globulin pattern of serum in $alpha_1$-antitrypsin deficiency. Scand J Clin Lab Invest 15:132–140, 1963.
5. Cantor J O, Cerreta J M, Armand G, Keller S, Turino G M: Pulmonary air-space enlargement induced by intratracheal instillment of hyaluronidase and concomitant exposure to 60% oxygen. Exper Lung Res 19:177–192, 1993.
6. Cantor J O, Cerreta J M, Keller S, Turino G M. Modulation of airspace enlargement in elastase-induced emphysema by intratracheal instillment of hyaluronidase and hyaluronic acid. Exp Lung Res. 1995;21:423–436.
7. Anthony N, Belder D E, Owe Wik K. Preparation and properties of fluorescein-labeled hyaluronate. Carbohyd Res. 1975;44;251–257.
8. Cantor J O, Willhite M, Bray B A, Keller S, Mandl I, Turino G M. Synthesis of crosslinked elastin by a mesothelial cell culture. Proc Soc Exp Biol Med 181:387–391, 1986.
9. Bray B A, Hsu W, Turino G M. Lung hyaluronan as assayed with a biotinylated hyaluronan-binding protein. Exp Lung Res. 1994;20:317–330.
10. Baccarani-Contri M, Vincenzi D, Cicchetti F, Mori G, Pasquali-Ronchetti I. Immunocytochemical localization of proteoglycans within normal elastin fibers. Eur J Cell Biol. 1990;53:305–312.
11. Campbell E J, Senior R M, McDonald J A, Cox D L. Proteolysis by neutrophils: Relative importance of cell-substrate contact and oxidative inactivation of proteinase inhibitors in vitro. J Clin Invest 70:845–852, 1982.
12. Bhattacharya J, Cruz T, Bhattacharya S, Bray B. Hyaluronan affects extravascular water in lungs of unanesthetized rabbits. J Appl Physiol. 1989;66:2595–2599.

13. Toole B P. Glycosaminoglycans and morphogenesis. In: Hay ED, ed, Cell Biology of Extracellular Matrix. New York: Plenum; 1981:259–294.
14. Leardini G, Mattara L, Franceschini M, Perbellini A. Intra-articular treatment of knee osteoarthritis. A comparative study between hyaluronic acid and 6-methyl prednisolone acetate. Clin Exp Rheum. 1991;9:375–381.
15. Graf J, Neusel E, Schneider E, Niethard F U. Intra-articular treatment with hyaluronic acid in osteoarthritis of the knee joint: a controlled clinical trial versus muco-polysaccharide polysulfuric acid ester. Clin Exp Rheum. 1993; 11:367–372.
16. Aviad A D. The molecular weight of therapeutic hyaluronan (sodium hyaluronate): how significant is it? J Rheum. 1994;21:297–301.
17. King S R, Hickerson W L, Proctor K G. Beneficial actions of exogeneous HA on wound healing. Surgery. 1991;109:76–84.
18. Goldberg EP, Burns JW, Yaacobi Y. Prevention of postoperative adhesion by precoating tissues with dilute sodium hyaluronate solutions. Prog Clin Biol Res. 1993;381:191–204.

What is claimed is:

1. A method of preventing tissue elastic fiber injury in the lung which comprises administering to a mammal a therapeutically effective amount of hyaluronic acid that covalently or noncovalently binds to and coats elastic fibers, thereby preventing enzymes, oxidants, or other injurious agents from contacting and damaging these fibers.

2. A method of claim 1, wherein the administration is performed intratracheally by aerosolization.

3. A method of claim 2, wherein the aerosol is generated by a nebulizer.

4. A method of claim 1, wherein the administration is performed by application to the skin, subcutaneous injection, intravenous injection, oral ingestion, intramuscular injection, anal suppository or internal topical application.

5. A method of claim 1, wherein the mammal is a human.

6. A method of claim 1, wherein the hyaluronic acid is administered with a suitable carrier.

7. A method of claim 6, wherein the carrier is saline solution, DMSO, alcohol, or water.

8. A method of claim 1, wherein hyaluronic acid is from about 0.1 $\mu$g/kg body wt per day to about 1 mg/kg body wt per day.

* * * * *